(12) United States Patent
Wen et al.

(10) Patent No.: US 7,882,748 B2
(45) Date of Patent: Feb. 8, 2011

(54) CLIP FOR DETECTING BENDING FORCES AND ELECTRICAL CHARACTERISTICS

(75) Inventors: Bor-Jiunn Wen, Hsinchu (TW);
Hsin-Da Yeh, Hsinchu (TW);
Cheng-Hsien Chen, Chiayi (TW);
Hsin-Yi Ko, Taipei (TW); Zong-Ying Chung, Kaohsiung (TW)

(73) Assignee: Industrial Technology Research Institute, Hsin-Chu (TW)

( * ) Notice: Subject to any disclaimer, the term of this patent is extended or adjusted under 35 U.S.C. 154(b) by 211 days.

(21) Appl. No.: 12/399,325

(22) Filed: Mar. 6, 2009

(65) Prior Publication Data

US 2010/0116064 A1 May 13, 2010

(30) Foreign Application Priority Data

Nov. 11, 2008 (TW) ............................... 97143456 A

(51) Int. Cl.
*G01N 3/20* (2006.01)
(52) U.S. Cl. .......................................... 73/849; 73/760
(58) Field of Classification Search .................. 73/760, 73/849, 852, 856
See application file for complete search history.

(56) References Cited

U.S. PATENT DOCUMENTS

| | | | |
|---|---|---|---|
| 3,602,866 A * | 8/1971 | Saxl ............................... 338/5 |
| 4,203,810 A | 5/1980 | Warne et al. | |
| 4,489,586 A * | 12/1984 | Hess ........................... 72/389.3 |
| 4,489,652 A * | 12/1984 | Takeuchi et al. ............. 101/211 |
| 5,329,597 A * | 7/1994 | Kouno et al. ................. 382/152 |
| 5,652,805 A * | 7/1997 | Ooenoki et al. .............. 382/141 |
| 5,680,217 A * | 10/1997 | Yli-Vakkuri ................. 356/602 |
| 6,581,456 B1 | 6/2003 | Clark | |
| 7,096,743 B2 | 8/2006 | Vogel et al. | |
| 7,181,979 B1 | 2/2007 | Lin et al. | |
| 7,383,715 B2 * | 6/2008 | Kutschker ..................... 72/422 |
| 7,387,035 B2 | 6/2008 | Struckmeier et al. | |
| 7,605,966 B2 * | 10/2009 | Tani et al. ................. 359/224.1 |

FOREIGN PATENT DOCUMENTS

| | | |
|---|---|---|
| TW | I279560 | 4/2007 |
| TW | 200724890 | 7/2007 |
| TW | I291047 | 12/2007 |

* cited by examiner

*Primary Examiner*—Max Noori
(74) *Attorney, Agent, or Firm*—WPAT, PC; Justin King

(57) ABSTRACT

A clip for detecting bending forces and electrical characteristics is disclosed, which comprises: a base; a clipping head fixedly disposed on the base and composed of a clipping sheet and a fixing sheet combined therewith; and a force detecting unit fixedly disposed the base and contacting the clipping head; wherein the clipping head is provided with two electrodes thereon and the two electrodes contact a substrate when the clipping head clips the substrate.

22 Claims, 5 Drawing Sheets

CLIP FOR DETECTING BENDING FORCES AND ELECTRICAL CHARACTERISTICS

FIELD OF THE INVENTION

The present invention generally relates to a clip and, more particularly, to a clip capable of detecting bending forces and electrical characteristics.

BACKGROUND OF THE INVENTION

In recent years, with the advancement in semiconductor and displays, various electronic products such as handsets, notebook computers and digital home appliances have evolved so that these electronic products are now compact, portable and convenient. For some electronic products with a large display required for viewing, the size is large and thus is not readily portable. Therefore, flexible displays are provided. However, the optical, mechanical and electrical characteristics of such flexible displays are rarely seen in some reports. Accordingly, it has become crucial to define flexibility of flexible devices by theories and experiments and provide a reliable flexible mechanism with quantized flexibility so as to detect optical, mechanical or electrical characteristics detecting of a bended or warped object.

There are two methods for measuring bending forces of a flexible device. One is by optical measurement, for example, U.S. Pat. No. 4,263,810 and U.S. Pat. No. 7,387,035 and the other is by contact-type measurement, for example, U.S. Pat. Nos. 6,581,456, 7,096,743 and Taiwan Pat. Pub. No. 200724890.

For electrical characteristics measurement, in Taiwan Pat. No. I279560, Taiwan Pat. No. I291047 and U.S. Pat. No. 7,181,979, electrical characteristics on the surface of flexible devices are measured. More particularly, in Taiwan Pat. No. I291047 and U.S. Pat. No. 7,181,979, a roll-to-roll mechanism is used with electrodes to build up an electrical field while the flexible devices are being manufactured or measured to detect electrical characteristics.

However, in the above mentioned techniques, electrical and optical characteristics cannot be measured at the same time.

SUMMARY OF THE INVENTION

The present invention provides a clip for detecting bending forces and electrical characteristics, the clip comprising: a base; a clipping head, fixedly disposed on the base and composed of a clipping sheet and a fixing sheet combined therewith; and at least one force detecting unit, fixedly disposed on the base and contacting the clipping head; wherein the clipping head is provided with two electrodes thereon and the two electrodes contact a substrate when the clipping head clips the substrate.

The present invention further provides a clip module for detecting bending forces and electrical characteristics, the clip module comprising: a first clip, comprising: a first base; a first clipping head, fixedly disposed on the first base and composed of a first clipping sheet and a first fixing sheet combined therewith; and a first force detecting unit, fixedly disposed on the first base and contacting the first clipping head; a second clip, comprising: a second base; a second clipping head, fixedly disposed on the second base and composed of a second clipping sheet and a second fixing sheet combined therewith; and a third force detecting unit, fixedly disposed on the second base and contacting the second clipping head; wherein the first clipping head and the second clipping head are respectively provided with two electrodes thereon and the two electrodes contact a substrate when the first clipping head and the second clipping head clip the substrate respectively.

BRIEF DESCRIPTION OF THE DRAWINGS

The objects and spirits of various embodiments of the present invention will be readily understood by the accompanying drawings and detailed descriptions, wherein.

DETAILED DESCRIPTION OF THE PREFERRED EMBODIMENT

Figure 1:
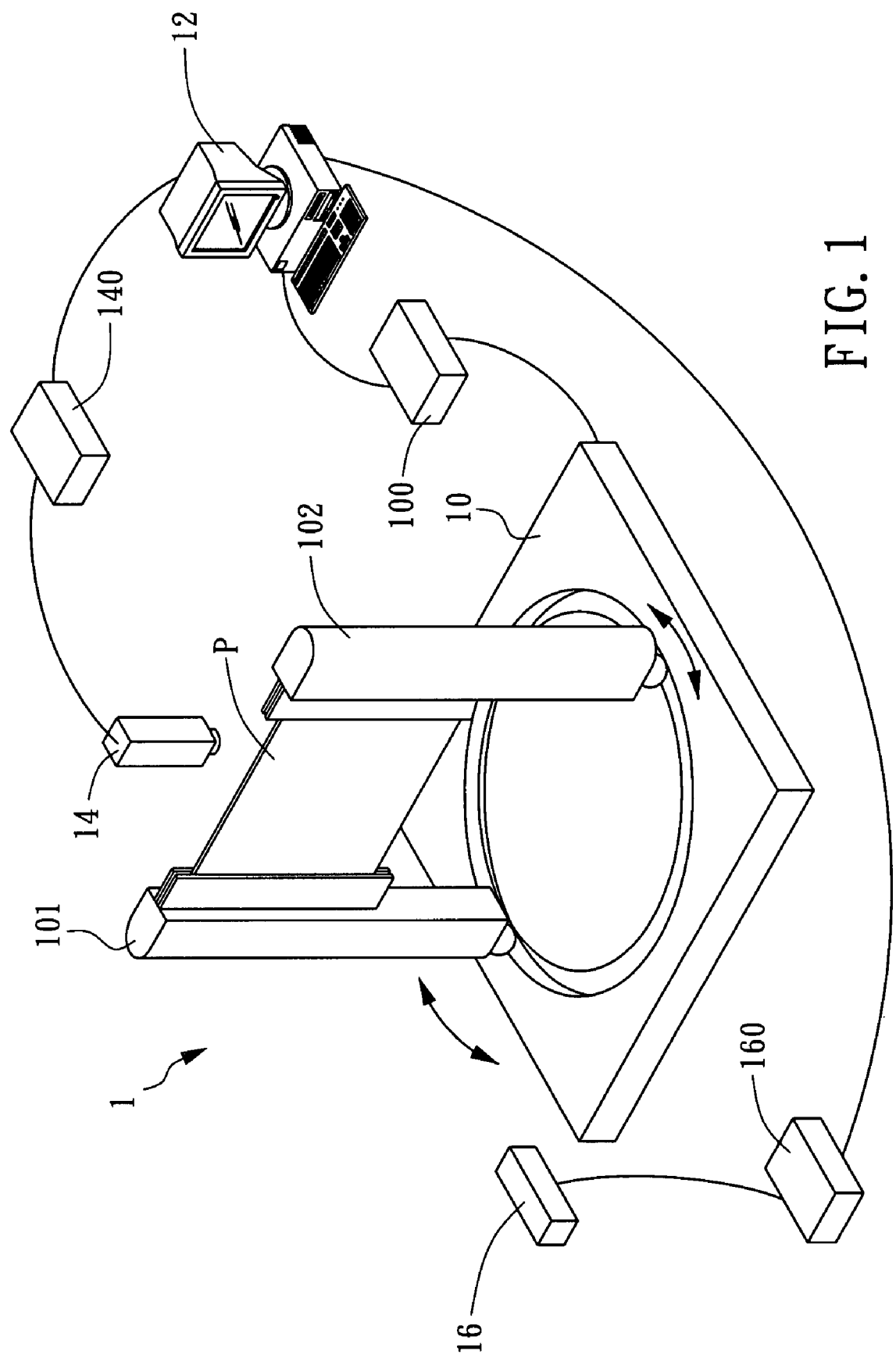
FIG. 1 is a conventional system for detecting characteristics of a flexible device.

The present invention can be exemplified but not limited by the embodiments as described hereinafter.

The clip for detecting bending forces and electrical characteristics of present invention is usable in a system capable of detecting characteristics of flexible devices. The system is shown, for example, in FIG. 1. The system 1 for detecting characteristics of flexible devices comprises a clipping device 10, a computer 12, a CCD camera 14 and a detecting device 16. The clipping device 10 is electrically connected to the computer 12 through a movable controller 100. The CCD Camera 14 is also electrically connected to the computer 12 through a movable controller 140. The detecting device 16 is also electrically connected to the computer 12 through a movable controller 160. In other words, the computer 12 controls the clipping device 10, the CCD Camera 14 and the detecting device 16 through the movable controller 100, the movable controller 140 and the movable controller 160, respectively. The clipping device 10 is provided with two clipping arms 101 and 102 thereon for clipping a substrate P under test. The substrate P under test is a sheet or a plate.

In operation, the computer 12 controls the CCD Camera 14 through the movable controller 140 so that the CCD Camera 14 moves to one side of the substrate P under test to detect the surface profile of the substrate P under test and send detected data back to the computer 12. Moreover, the computer 12 also controls the detecting device 16 through the movable controller 160 so that detecting device 16 moves towards the substrate P under test and stops at a distance to detect the variation of characteristics of the substrate P under test, for example, optical characteristics (the luminance and the chrominance), mechanical characteristics (surface defects and deformation) and/or electrical characteristics.

Figure 2:
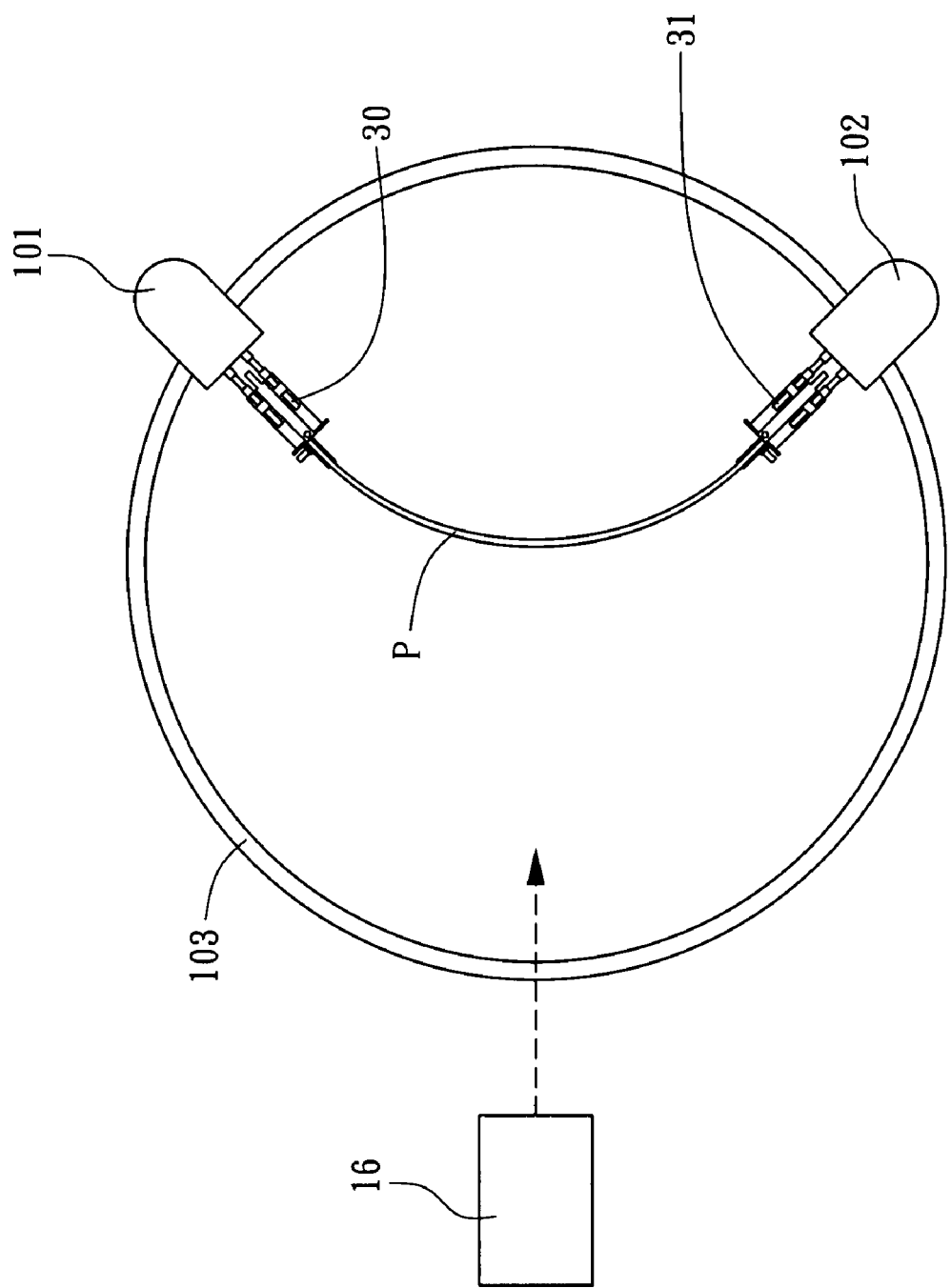
FIG. 2 is a top view of FIG. 1.

FIG. 2 is a top view of FIG. 1, wherein some components are omitted. In FIG. 2, the clipping arms 101 and 102 are respectively provided with a first clip 30 and a second clip 31 so as to clip and bend the substrate P under test.

Figure 3:
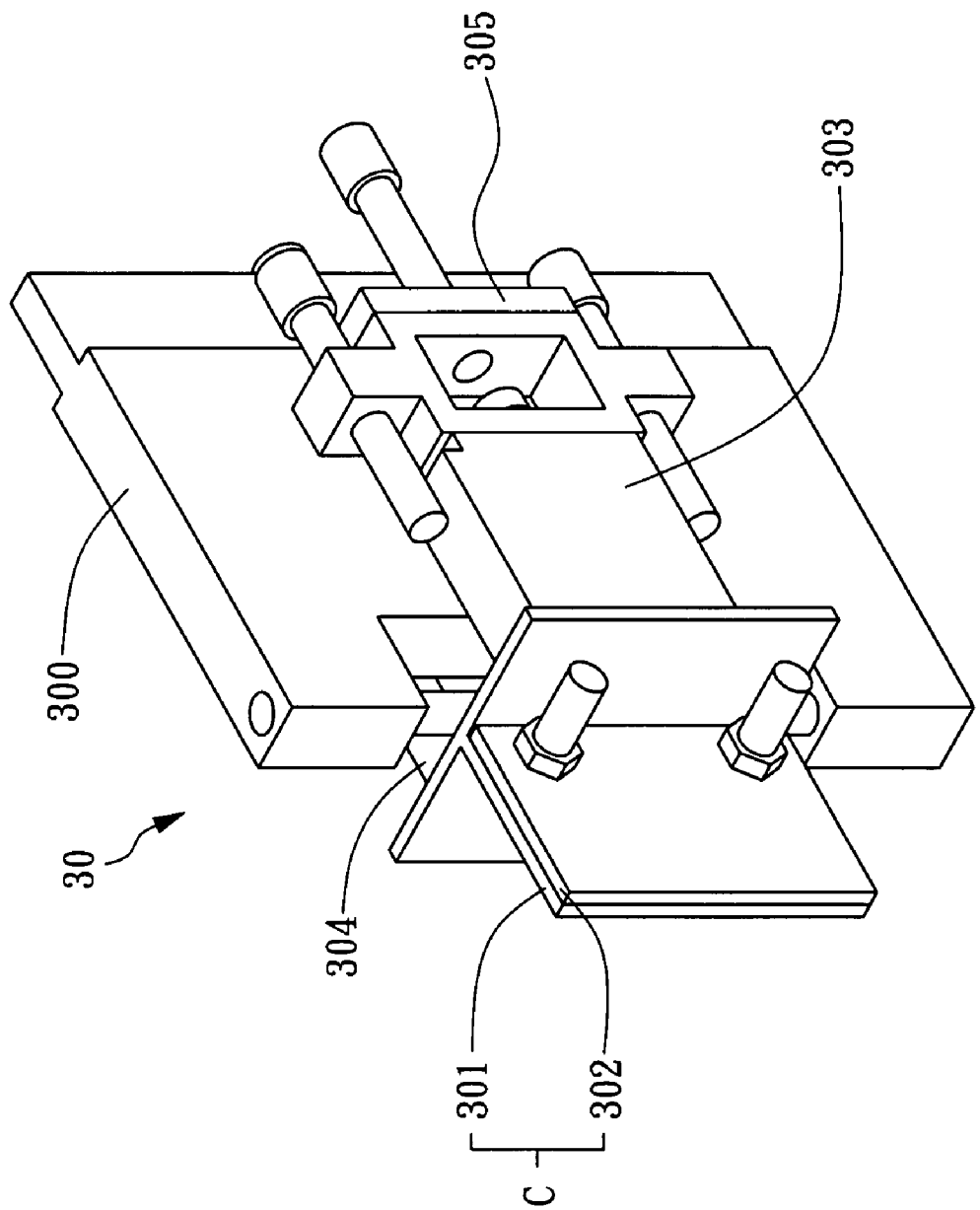
FIG. 3 is 3-D view of a clip for detecting bending forces and electrical characteristics according to one embodiment of the present invention.
Figure 4:
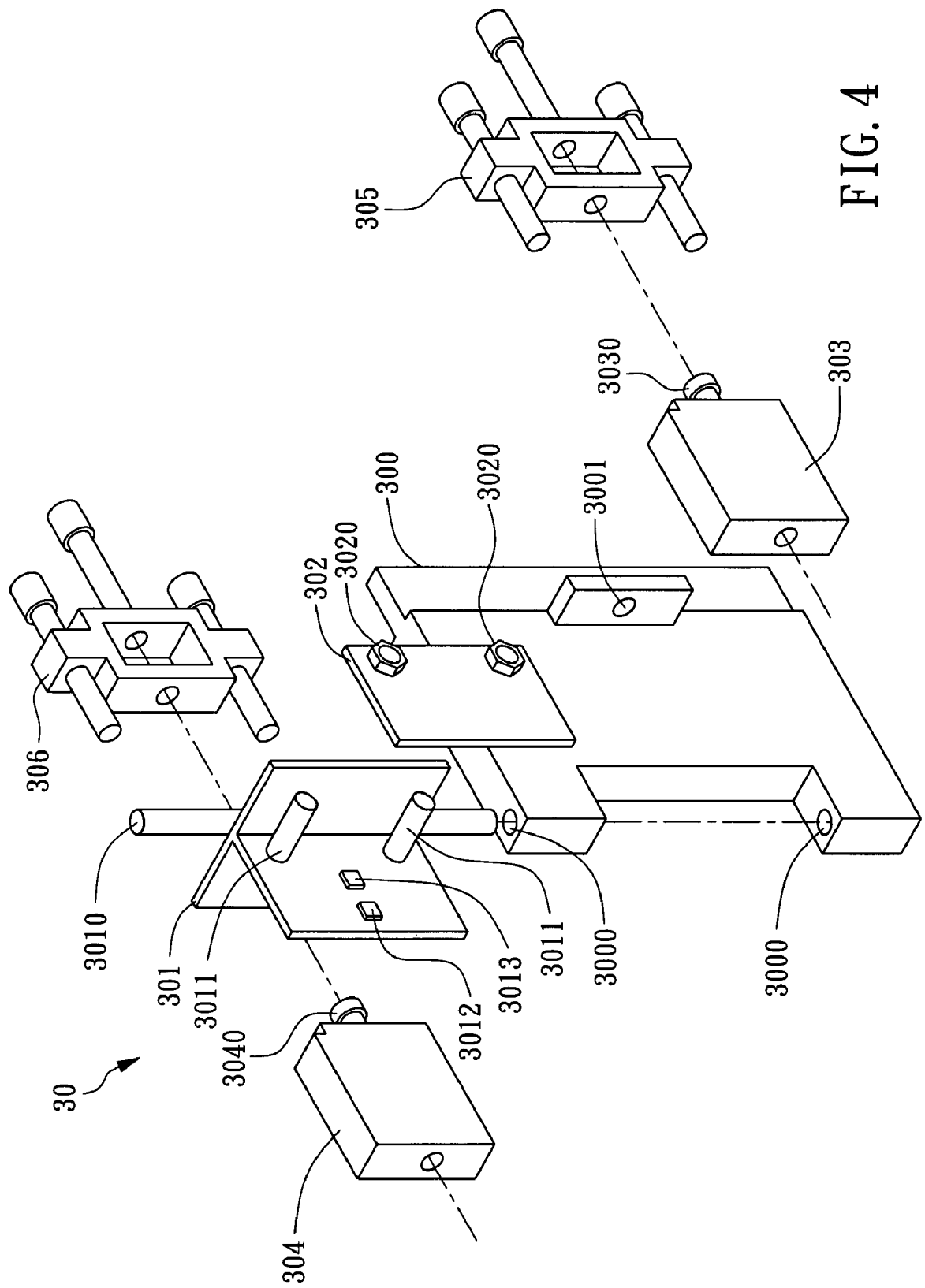
FIG. 4 is an exploded view of a clip for detecting bending forces and electrical characteristics according to one embodiment of the present invention.

FIG. 3 is a 3-D view of a clip for detecting bending forces and electrical characteristics according to one embodiment of the present invention;

FIG. 4 is an exploded view of a clip for detecting bending forces and electrical characteristics according to one embodiment of the present invention;

Please refer to FIG. 3 and FIG. 4 for a 3-D view and an exploded view of a clip for detecting bending forces and electrical characteristics according to one embodiment of the present invention, respectively. In the present embodiment, the clip 30 comprises a base 300, a clipping head C, a first force detecting unit 303, a second force detecting unit 304, a first fine-tuning unit 305 and a second fine-tuning unit 306.

The clipping head C comprises a clipping sheet 301 and a fixing sheet 302 combined therewith. The clipping sheet 301 uses a hinge 3010 to penetrate a hole 3000 on the base 300 and is thus fixedly disposed on base 300. The clipping sheet 301 is provided with at least one protruding screw bolt 3011 thereon. The fixing sheet 302 is provided with at least one screw nut 3020 corresponding to the at least one screw bolt 3011. As the screw bolt 3011 penetrates the fixing sheet 302, it is thus fixed by the screw nut 3020. Alternatively, in addition to the screw bolt, the clipping sheet 301 and the fixing sheet 302 can be combined by a fastener. Moreover, the clipping sheet 301 is provided with electrodes 3012 and 3013. As the clipping head C (i.e., the clipping sheet 301 and the fixing sheet 302) clips the substrate under test (not shown), the electrodes 3012 and 3013 contact the substrate under test. The first force detecting unit 303 and the second force detecting unit 304 are fixedly disposed on two opposite sides of the base 300. Moreover, the first force detecting unit 303 and the second force detecting unit 304 contact the clipping sheet 301. Moreover, the first force detecting unit 303 is combined with the first fine-tuning unit 305 by a screw bolt 3030. More particularly, the fine-tuning unit 305 is firstly fixedly disposed in the screw hole 3001 on the base 300, and then the first force detecting unit 303 is combined with the first fine-tuning unit 305 by the screw bolt 3030. The second force detecting unit 304 is combined with the second fine-tuning unit 306 by a screw bolt 3040. Certainly, the first fine-tuning unit 305 and the second fine-tuning unit 306 can be firstly disposed on the base 300, and then are respectively combined with the first force detecting unit 303 and the second force detecting unit 304.

Figure 5:
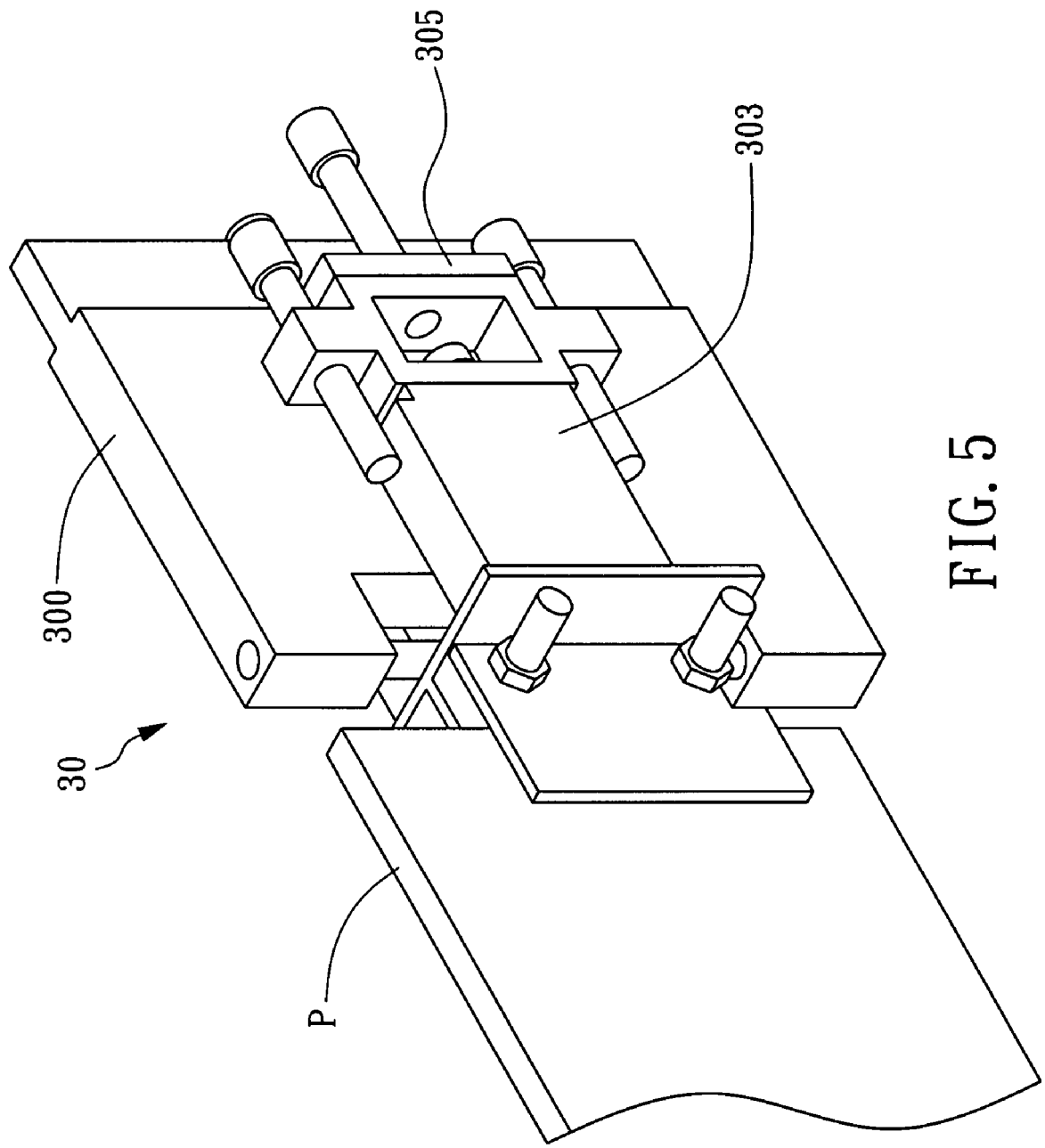
FIG. 5 is a schematic view of a clip for detecting bending forces and electrical characteristics of a substrate under test according to one embodiment of the present invention.

Accordingly, as the clip 30 clips the substrate P under test using the clipping head, as shown in FIG. 5, the bending force of the substrate P under test can be detected because the tension/restoring force of the substrate P under test is applied on the first force detecting unit 303 or the second force detecting unit 304 through the clipping head. To measure the electrical characteristics (for example, the resistance) of the substrate P under test, a current is injected into the substrate P under test and then the current and the voltage of the substrate P under test are measured at the electrodes 3012 and 3013 of the clip 30. Similarly, the current and the voltage can also be measured at the two electrodes of the clip 31 (not shown) clipping on the other end of the substrate P under test. Therefore, the current and the voltage on both ends of the substrate P under test can be obtained. Moreover, the resistance of the substrate P under test can be calculated based on the current and the voltage so that electrical characteristics are obtained.

Accordingly, the present invention provides a clip for detecting bending forces and electrical characteristics using the bending force measuring mechanism to define the conditions for measuring flexibility when the radius of curvature of the flexible device cannot be used to define flexibility. Parameters corresponding to flexibility defined in the present invention are very useful in detecting optical, mechanical or electrical characteristics of a warping or flexible substrate.

Although this invention has been disclosed and illustrated with reference to particular embodiments, the principles involved are susceptible for use in numerous other embodiments that will be apparent to persons skilled in the art. This invention is, therefore, to be limited only as indicated by the scope of the appended claims.

What is claimed is:

1. A clip for detecting bending forces and electrical characteristics, the clip comprising:
   a base;
   a clipping head, fixedly disposed on the base and composed of a clipping sheet and a fixing sheet combined therewith; and
   at least one force detecting unit, fixedly disposed on the base and contacting the clipping head;
   wherein the clipping head is provided with two electrodes thereon and the two electrodes contact a substrate when the clipping head clips the substrate.

2. The clip for detecting bending forces and electrical characteristics as recited in claim 1, wherein the at least one force detecting unit comprises a first force detecting unit fixedly disposed on the base and contacting the clipping head and a second force detecting unit fixedly disposed on the base and contacting the clipping head.

3. The clip for detecting bending forces and electrical characteristics as recited in claim 2, wherein the first force detecting unit and the second force detecting unit are disposed respectively on two opposite sides of the base.

4. The clip for detecting bending forces and electrical characteristics as recited in claim 1, wherein the clipping sheet and the fixing sheet are combined by a screw bolt disposed therebetween.

5. The clip for detecting bending forces and electrical characteristics as recited in claim 1, wherein the clipping sheet and the fixing sheet are combined by a fastener disposed therebetween.

6. The clip for detecting bending forces and electrical characteristics as recited in claim 1, further comprising a fine-tuning unit combined with the force detecting unit.

7. The clip for detecting bending forces and electrical characteristics as recited in claim 6, wherein the fine-tuning unit and the force detecting unit are combined by a screw bolt disposed therebetween.

8. The clip for detecting bending forces and electrical characteristics as recited in claim 6, wherein the fine-tuning unit is installed on the base.

9. A clip module for detecting bending forces and electrical characteristics, the clip module comprising:
   a first clip, comprising:
      a first base;
      a first clipping head, fixedly disposed on the first base and composed of a first clipping sheet and a first fixing sheet combined therewith; and
      a first force detecting unit, fixedly disposed on the first base and contacting the first clipping head;
   a second clip, comprising:
      a second base;
      a second clipping head, fixedly disposed on the second base and composed of a second clipping sheet and a second fixing sheet combined therewith; and
      a third force detecting unit, fixedly disposed on the second base and contacting the second clipping head;
   wherein the first clipping head and the second clipping head are respectively provided with two electrodes thereon and the two electrodes contact a substrate when the first clipping head and the second clipping head clip the substrate respectively.

10. The clip module for detecting bending forces and electrical characteristics as recited in claim 9, wherein the first clip further comprises a second force detecting unit fixedly disposed on the first base and contacting the first clipping head and the second clip further comprises a fourth force detecting unit fixedly disposed on the second base and contacting the second clipping head.

11. The clip module for detecting bending forces and electrical characteristics as recited in claim 10, wherein the first force detecting unit and the second force detecting unit are disposed respectively on two opposite sides of the first base.

12. The clip module for detecting bending forces and electrical characteristics as recited in claim 10, wherein the third force detecting unit and the fourth force detecting unit are disposed respectively on two opposite sides of the second base.

13. The clip module for detecting bending forces and electrical characteristics as recited in claim 9, wherein the first clipping sheet and the first fixing sheet are combined by a screw bolt disposed therebetween.

14. The clip module for detecting bending forces and electrical characteristics as recited in claim 9, wherein the first clipping sheet and the first fixing sheet are combined by a fastener disposed therebetween.

15. The clip module for detecting bending forces and electrical characteristics as recited in claim 9, wherein the second clipping sheet and the second fixing sheet are combined by a screw bolt disposed therebetween.

16. The clip module for detecting bending forces and electrical characteristics as recited in claim 9, wherein the second clipping sheet and the second fixing sheet are combined by a fastener disposed therebetween.

17. The clip module for detecting bending forces and electrical characteristics as recited in claim 9, further comprising a first fine-tuning unit combined with the first force detecting unit.

18. The clip module for detecting bending forces and electrical characteristics as recited in claim 17, wherein the first fine-tuning unit and the first force detecting unit are combined by a screw bolt.

19. The clip module for detecting bending forces and electrical characteristics as recited in claim 17, wherein the first fine-tuning unit is installed on the first base.

20. The clip module for detecting bending forces and electrical characteristics as recited in claim 9, further comprising a second fine-tuning unit combined with the third force detecting unit.

21. The clip module for detecting bending forces and electrical characteristics as recited in claim 20, wherein the second fine-tuning unit and the first force detecting unit are combined by a screw bolt.

22. The clip module for detecting bending forces and electrical characteristics as recited in claim 20, wherein the second fine-tuning unit is installed on the second base.

* * * * *